(12) United States Patent
Garcia Tello et al.

(10) Patent No.: US 8,813,777 B2
(45) Date of Patent: Aug. 26, 2014

(54) FLUID SEPARATION STRUCTURE AND A METHOD OF MANUFACTURING A FLUID SEPARATION STRUCTURE

(75) Inventors: Pablo Garcia Tello, Leuven (BE); Vijaraghavan Madakasira, Louvain (BE)

(73) Assignee: NXP, B.V., Eindhoven (NL)

( * ) Notice: Subject to any disclaimer, the term of this patent is extended or adjusted under 35 U.S.C. 154(b) by 494 days.

(21) Appl. No.: 12/594,632

(22) PCT Filed: Apr. 17, 2008

(86) PCT No.: PCT/IB2008/051479
§ 371 (c)(1),
(2), (4) Date: Oct. 5, 2009

(87) PCT Pub. No.: WO2008/126064
PCT Pub. Date: Oct. 23, 2008

(65) Prior Publication Data
US 2010/0116656 A1   May 13, 2010

(30) Foreign Application Priority Data

Apr. 17, 2007  (EP) .................................. 07106344

(51) Int. Cl.
*F15C 1/06*   (2006.01)
(52) U.S. Cl.
USPC ............ 137/545; 137/833; 977/782; 977/890

(58) Field of Classification Search
CPC .................. F16K 2099/0074; B01L 2200/025; B01J 2219/00659; G01N 27/44791; B82Y 40/00; B82Y 15/00; C01P 2400/16; B81C 1/00031
USPC ................... 137/833, 545; 977/782, 888–893
See application file for complete search history.

(56) References Cited

U.S. PATENT DOCUMENTS

| 5,976,957 | A | * | 11/1999 | Westwater et al. ........... 438/478 |
| 6,091,148 | A | * | 7/2000 | Givens et al. ................. 257/750 |
| 2002/0081744 | A1 | | 6/2002 | Chan et al. |
| 2003/0119034 | A1 | | 6/2003 | Kang |
| 2006/0035386 | A1 | | 2/2006 | Hattori et al. |
| 2006/0177350 | A1 | | 8/2006 | Sano et al. |

FOREIGN PATENT DOCUMENTS

| EP | 1217366 | A2 | 6/2002 |
| JP | 2003315349 | A | 11/2003 |
| JP | 2004045357 | A | 2/2004 |
| JP | 2004-317340 | | 11/2004 |
| WO | 0163273 | A2 | 8/2001 |
| WO | 2005001021 | A2 | 1/2005 |

OTHER PUBLICATIONS

Inatomi, Ken-Ichi, et al; "Electrophoresis of DNA in Micro-Pillars Fabricated in Polydimethylsiloxane"; Microelectronic Engineering; vol. 70, Issue 1; pp. 13-18; 2003.

(Continued)

*Primary Examiner* — J. Christopher Ball

(57) ABSTRACT

An electrophoretic fluid separation structure (100) comprising a substrate (101) and a plurality of vertical nanowires (102) grown on the substrate (101).

16 Claims, 3 Drawing Sheets

(56) References Cited

OTHER PUBLICATIONS

Hattori, W., et al; "Size-Based Continuous-Flow Directional Conrol of DNA With a Nano-Pillar Anisotropic Array"; Journal of Chromatography; Elsevier Science Publishers B.V.; Amserdam, NL; vol. 1051, No. 1-2; Oct. 8, 2004; pp. 141-146; XP004587109; ISSN: 0021-9673.

Cabodi, M., et al; "Entropic Recoil Separation of Long DNA Molecules"; Analytical Chemistry; American Chemical Society, Columbus, OH; US; vol. 20, No. 74; Oct. 15, 2004; pp. 5169-5174; XP001141014; ISSN: 003-2700.

Ogawa, et al; "Fabrication on Nano-Pillar Chips by a Plasma Etching Technique for Fast DNA Separation"; Thin Solid Films, Elsevier-Sequoia S.A., Lausanne, CH; vol. 515, No. 12; Nov. 27, 2006; pp. 5167-5171; XP022212204; ISSN: 0040-6090.

Kaji, N., et al; "Separation of Long DNA Molecules by Quartz Nanopillar Chips Under a Direct Current Electric Filed"; Analytical Chemistry; American Chemical Society; Columbus, OH, US; vol. 76, No. 1; Jan. 1, 2004; pp. 15-22; XP001047450; ISSN: 0003-2700.

\* cited by examiner

FLUID SEPARATION STRUCTURE AND A METHOD OF MANUFACTURING A FLUID SEPARATION STRUCTURE

FIELD OF THE INVENTION

The invention relates to a fluid separation structure.

Moreover, the invention relates to a method of manufacturing a fluid separation structure.

Beyond this, the invention relates to a method of using a fluid separation structure for separating components of a fluidic sample.

BACKGROUND OF THE INVENTION

Separation of components (such as biomolecules, for instance DNA) of a fluidic sample becomes more and more important for medical applications, biochemistry, food chemistry, etc.

Conventional separation approaches such as gel electrophoresis or capillary electrophoresis become problematic when being applied to very small volumes of a biological sample.

Ken-ichi Inatomi et al. (2003) "Electrophoresis of DNA in micro-pillars fabricated in polydimethylsiloxane", Microelectronic Engineering, Volume 70, Issue 1, pages 13 to 18 discloses the fabrication of a device containing micro-pillars for separation of DNA. It is made of polydimethylsiloxane (PDMS) and is manufactured by a replica molding method using a patterned silicon wafer as a mold. The device has a micro-channel in which 15 µm pillars are arranged in a hexagonal lattice with 1 µm spacing. Electrophoresis of DNA in the pillars showed that the average speed of DNA migration is dependent on its lengths.

However, a sufficient quality and reproducibility of the manufactured devices cannot be guaranteed due to the very nature of the fabrication process employed by Ken-ichi Inatomi et al. (2003). Furthermore, it would be very difficult to manufacture such devices on an industrial scale, as it will become clear in further sections below.

OBJECT AND SUMMARY OF THE INVENTION

It is an object of the invention to provide a fluid separation structure being manufacturable with a proper quality.

In order to achieve the object defined above, a fluid separation structure, a method of manufacturing a fluid separation structure, and a method of using a fluid separation structure for separating components of a fluidic sample according to the independent claims are provided.

According to an exemplary embodiment of the invention, a fluid separation structure (which may be adapted for separating, for instance by electrophoresis or dielectrophoresis, different components of a fluidic sample comprising a mix of different components differing regarding at least one physical parameter such as length) is provided comprising a substrate and a plurality of nanowires grown on the substrate.

According to another exemplary embodiment of the invention, a method of manufacturing a fluid separation structure is provided, the method comprising growing a plurality of nanowires on a substrate.

According to still another exemplary embodiment of the invention, a fluid separation structure having the above mentioned features may be used for separating different components/fractions of a fluidic sample.

The term "substrate" may denote any suitable material, such as a semiconductor, glass, plastic, etc. According to an exemplary embodiment, the term "substrate" may be used to define generally the elements for layers that underlie and/or overlie a layer or portions of interest. Also, the substrate may be any other base on which a layer is formed, for example a semiconductor wafer such as a silicon wafer or silicon chip. A portion of the substrate on which nanowires are grown may be a two-dimensional (essentially) planar surface. The substrate surface may be a template for a subsequent growing procedure of the nanowires. Since the growth of nanowires may be efficiently triggered or spatially controlled by appropriate materials (for instance iron or nickel spots may catalyze the growth of carbon nanotubes), an accurate spatial control of growth positions may be accurately defined.

The term "nanowire" may denote a post-like structure having dimensions in the order of magnitude of several to several thousands of nanometers (and may also cover larger or smaller dimensions). An array of closely neighboured nanowires may serve as an array of mechanical barriers for (macro-) molecules of a sample and may therefore serve as a fluid separation structure, since the barrier-effect of the array is different for differently sized particles of the fluidic sample. Many different types of nanowires may be used for embodiments of the invention, including semiconducting nanowires (for instance made of silicon, germanium, InP, GaN, etc.), metallic nanowires (for instance nickel, platinum, gold), and nanotubes, particularly carbon nanotubes (intrinsic or doped). Such a nanowire may be an oblong nanowire.

The term "oblong nanowire" may denote that the length of the nanowire is larger, particularly significantly larger, than a dimension perpendicular to the length extension. In other words, typical nanowires may exhibit aspect ratios (the ratio between length to width) of more than one, particularly of more than 2, more particularly of more than 5, or up to 1000 or more. For instance, a tubular nanowire may have a length of 50 nm to 70 nm and may have a diameter of 10 nm.

The term "fluidic sample" may particularly denote any subset of the phases of matter. Such fluids may include liquids, gases, plasmas and, to some extent, solids, as well as mixtures thereof. Examples for fluidic samples are DNA containing fluids, blood, interstitial fluid in subcutaneous tissue, muscle or brain tissue urine or other body fluids. For instance, the fluidic sample may be a biological substance. Such a substance may comprise proteins, polypeptides, nucleic acids, DNA strands, etc.

The term "fluid separation structure" may particularly denote any structure that allows separating different components of a fluidic sample, particularly to separate different components having different dimensions, for example different lengths. Thus, a fluid separation structure may also have the capability to move, in a defined manner, particles of a sample through an array of nanowires under the influence of a force, such as a mechanical force (for instance pressure or gravitation), an electric force, a magnetic force, etc. When operating such a fluid separation device, also parameters such as electrical parameters, for instance an electrical charge, of the different components, may also used for enhancing the fluid separation capabilities. For example, a distance of pillars of a net of pillars or nanowires may define a migration speed of particles being transported through such a net under the influence of an electrical force. Consequently, fractions of the fluidic sample having different sizes and/or electric properties may then be separated by the different values of their mobility in the web of nanowires.

According to an exemplary embodiment of the invention, an array of nanowires may be formed and may be directly grown on the substrate to serve as an arrangement of defined obstacles having a defined distance from one another, so that the capability of passing the obstacles (which capabilities depend on the size of the particles to be separated) may be used as a basis for a separation of different fluid fractions. Particularly, by directly growing the nanowires on the substrate (without the need to implement molding or lithography procedures), that is to say by forming the nanowires by a deposition of a structure directly on the substrate in a trenchless manner, it may be possible to manufacture robust nanowires that can be controlled in a spatially accurate manner, particularly by the deposition of specific catalyst spots on specific portions of the substrate. Therefore, a highly reliable, spatially accurate and mechanically robust structure may be formed and may be taken as a basis for a fluid separation application.

Thus, according to an exemplary embodiment of the invention, a patterned surface is provided for performing separation experiments, particularly for performing DNA separation.

Conventional techniques for DNA separation are inadequate for the rapidly growing demand for accurate, versatile, and portable devices for rapid genetic identification. This limitation arises due to the fact that conventional methods (based on gel or capillary electrophoresis) are tailored to separate DNA in a narrow size range. Moreover, these methods are limited to shorter fragments of DNA by the fundamental mesh size of the separation medium.

According to an exemplary embodiment of the invention, an easier way to manufacture a patterned and tailored nanosurface is provided that may significantly improve the performance regarding DNA separation, or in general of biomolecules of interest.

Exemplary embodiments of the invention may have the advantage that conventional CMOS fabrication techniques may be used. A fabrication scheme is provided which can be carried out in a simple manner. It may allow for an exact control of the characteristics of the nano-patterned surface. It may also provide for a possibility to integrate a pattern surface to any portable device aimed for the point of care use. A wide range of differently patterned surfaces can be fabricated in one run. Embodiments of the invention may further provide the opportunity to achieve method parallelism regarding DNA separation. Furthermore, embodiments of the invention may enable to be coupled to any of existing detection techniques (for instance fluorescence technique) to perform, for example, DNA sequencing.

Exemplary embodiments of the invention make use of the fact that the mobility of DNA molecules and electrophoretic characteristics may depend, among other factors, on the length of the DNA strain. In view of this recognition, according to an exemplary embodiment of the invention, a method of manufacturing a semiconductor device is provided for use in DNA separation by electrophoresis, wherein the device may comprise a semiconductor body. On the surface of the semiconductor body, at least one first pillar-shaped semiconductor region may be formed according to a first mesa structure. At least one second pillar-shape semiconductor region may be formed according to a second mesa structure.

According to an exemplary embodiment of the invention, a final coating of the pillar shaped semiconductor region (micropillars) may be performed with any desirable materials that present hydrophobic or hydrophilic properties that can be tailored to increase the device performance. Furthermore, patterning the surface is possible, wherein such a patterning may particularly allow defining hydrophobic and hydrophilic regions, thereby defining a route of the molecules along a surface of the fluid separation structure. Thus, a high performance medical device for molecular medicine applications may be provided.

According to an exemplary embodiment, a manufacturing method for a patterned device for separating DNA is provided. Nanowires may be grown on a substrate, a silicon oxide structure may be deposited on the nanowires, and the silicon oxide may be removed from the tip of the nanowires to expose an upper end portion of the nanowires. The remaining portion of the silicon oxide structure may serve as a mechanical reinforcement for the sensitive nanowires, whereas the exposure of the tip may refine the spatial resolution of the nanowire array.

The provision of nanowires such as nanotubes may allow improving the robustness of the separation web as compared to molding or lithographical post generation, since grown nanowires have specifically strong intrinsic chemical binding properties. In contrast to approaches in which pillars are fabricated using a replica molding method, the nanowire growing technique according to an exemplary embodiment of the invention may allow preventing a rapid degradation of the quality of the structure, and may guarantee a regular patterning. More particularly, the micropillars and possible microfluidic channels may be fabricated directly on a silicon wafer without the need of fabricating a molding first. This may allow for an exact control of the dimension due to the fact that no degradation of the microstructure is produced. In contrast to conventional molding fabrication techniques which do not enable a possible coating of micropillars and microfluidic channels because of the use of a single material (such as PDMS), embodiments of the invention provide a method of fabrication allowing for a final coating of the micropillars with any desirable material that may have hydrophobic or hydrophilic properties that can be configured to increase the device performance. Exemplary embodiments of the invention therefore allow for an easy coating (with hydrophobic or hydrophilic layers) of the nanofeatures. Thus, it is not necessary to perform coating after having formed the nanofeatures, which may involve limitations regarding the smallest size that is possible to achieve. Meanwhile, it is possible to easily perform a coating of the nanowires directly. According to an exemplary embodiment, it is sufficient that a single substrate is used, and no transfer from one substrate to another one is necessary, so that the device may be built up gradually with reasonable effort.

Very small geometric structures may be produced due to the use of nanowires that may be directly grown on a substrate. Furthermore, the fabrication flow can be easily integrated together in a standard CMOS procedure that allows for the fabrication of on-chip electronics at the same time.

Embodiments of the invention may overcome limitations of conventional systems to perform biomolecular separation and moreover may allow for the potential and easy fabrication of a fully versatile portable device that can be used in the point of care.

According to an exemplary embodiment, a device may be manufactured which is based on silicon nanowires that are grown on/in the substrate. By taking this measure, it is possible to obtain much smaller feature size because it is not necessary to rely on lithography but on the size of the nanowires themselves that are defined automatically by the process parameters. This may allow improving drastically the performance regarding a separation of biomolecules that may be extremely small and thus may increase the performance and versatility of the device.

Next, further exemplary embodiments of the fluid separation structure will be explained. However, these embodiments also apply to the method of manufacturing a fluid separation structure and to the method of use.

The fluid separation structure may comprise a cover structure partially covering the plurality of nanowires so that a tip of the plurality of nanowires is exposed. To manufacture such a fluid separation structure, it is possible to first deposit the nanowires on the substrate, to deposit afterwards the cover structure (for instance made of an electrically insulating material such as silicon oxide or silicon nitride) on the nanowires, and then to etch a portion of the cover structure so as to expose the tips of the nanowires. Then, the nanowires form some kind of carpet serving as mechanical obstacles for DNA molecules or other biomolecules to be detected. Such molecules have to pass the obstacles when moving along the array of nanowires, for instance under the influence of an electric force. Such a cover structure in which the nanowires may be partially embedded may improve the mechanical stability of the nanowires to thereby allow a use even under harsh conditions.

The plurality of nanowires may be grown to extend vertically from the substrate. For instance, it is possible to produce vertically arranged nanowires extending perpendicular to a main surface of the substrate by a growth, for instance on a catalysts template. Suitable catalysts for carbon nanotubes may be, for instance, iron or nickel.

The cover structure may partially cover the lateral side walls of the plurality of nanowires. Thus, the cover structure may give lateral support to the sensitive nanowires, thereby improving the mechanical stability of the entire fluid separation structure.

The cover structure may partially cover a surface of the substrate between the plurality of nanowires. Thus, the nanowires may not only be embedded on a stem portion by the lateral side walls, but may also be covered or embedded in a bottom structure, similar like a tree being stabilized in the ground. This may allow obtaining a networked nanowire system that is fixedly connected to the substrate.

The cover structure may comprise an electrically insulating material, particularly may comprise silicon oxide $SiO_2$ (or alternatively silicon nitride, $Si_3N_4$, or the like), more particularly may comprise a TEOS silicon oxide material and a High-Density Plasma (HDP) silicon oxide material. Such a two-component configuration of the cover structure comprising TEOS and HDP oxide may particularly form a very stable configuration with materials that are compatible to one another.

The substrate may comprise a semiconductor material, particularly may comprise one of the group consisting of a group IV semiconductor (such as silicon, germanium), and a group III-group V semiconductor (such as gallium arsenide). Silicon may be an appropriate choice, particularly a silicon wafer or a silicon chip, since this may allow integrating the manufacturing process in the CMOS technology. In such a context, the fluid separation structure may be configured as a monolithically integrated circuit.

The fluid separation structure may comprise a sample reservoir adapted for receiving a fluidic sample and to bring the fluidic sample in interaction with the plurality of particles. Such a sample reservoir may be a reception or a container formed in a manner that a fluidic sample to be analyzed can be brought in functional contact with the pillar structure, to thereby achieve a component separation feature.

The fluid separation structure may comprise an electric field generation unit adapted for generating an electric field for moving charged or polarisable particles of a fluidic sample along the plurality of nanowires. Such an electric field generation unit may comprise one or more electrodes that may be provided separately from the substrate or may be integrated within the substrate. Such electrodes may be operated in accordance with a voltage supply unit adapted for applying a particular voltage to the electrodes so that an electric field may be generated to define a motion path of the particles of the fluidic sample through the network of nanowires. Thus, under the influence of electrophoresis or dielectrophoresis, the particles may be moved along a predetermined direction so as to be brought in functional contact with the pillars. In accordance with the dimension of the different fractions of the fluidic sample, these will be capable to pass the pillar structure essentially without interference, or to be retained mechanically by the pillars. Therefore, the fluid may be separated into different fractions, in dependence of the size and other parameters such as an electric charge. This may be particularly advantageous for separating different fractions of a biochemical solution having a plurality of components, such as different DNA. Therefore, the structure may not only be used for fluid separation, but also for purification (for instance for isolating proteins from other components of a cell liquid), since different fractions may be separated from one another and may be, subsequently, treated independently from one another.

The fluid separation structure may further comprise a detection unit, particularly a fluorescence detection unit, adapted for detecting at least one fraction of particles of a fluidic sample separated from at least one further fraction of particles of a fluidic sample. Due to the different mobility of fractions having differently sized particles, the fluidic sample will be separated in a plurality of fractions that may subsequently pass a detection area. In this detection area, an electromagnetic radiation generator may be provided, for instance a light source, to provide excitation light to excite fractions of the particles or labels (such as fluorescence labels) attached thereto. In accordance with the presence of specific particles (and therefore specific labels) the light absorption, reflection and/or fluorescence properties may change when different fractions are in the focus of the detection unit. By taking this measure, a detection of individual fractions may be performed efficiently.

The plurality of nanowires may be arranged to form a two-dimensional array of nanowires. For instance, the nanowires may be arranged in rows and columns so as to form a matrix-like configuration.

Particularly, the two-dimensional array of nanowires may comprise a plurality of portions. A distance between adjacent nanowires differs in different ones of the plurality of portions. In other words, the mesh width may be different in different portions, so that portions with a high density of pillars may be provided next to a portion having a lower density of the pillars. By taking this measure, the separation functionality may be further refined.

The plurality of nanowires may be grown on a planar surface of the substrate, particularly may be grown on catalyst spots provided on the substrate. Therefore, an arrangement of catalyst spots or locations may first be defined on the fluid separation structure. Then, for instance by CVD (chemical vapour deposition), carbon nanotubes may be formed specifically on these spots. Therefore, the spatial definition of the pillar structure may be provided with high accuracy. However, it is also possible to define recesses in the substrate (which may or may not be provided with a catalyst material) and to start the growing procedure in the recesses.

A height of the plurality of nanowires may be less than or equal to 50 µm, particularly may be in a range between 5 µm and 50 µm. By such a pillar length, a powerful separation of components of a fluidic sample is possible even under the presence of very small sample volumes, making the device appropriate for many applications.

A diameter of the nanowires may be less than or equal to 100 nm, particularly may be less than 20 nm, more particularly may be less than 10 nm.

A distance between adjacent ones of the plurality of nanowires may be less than or equal to 2 μm, particularly may be in a range between 100 nm and 2 μm. This range has turned out to be highly appropriate for fluid separation of DNA, proteins, etc., since the dimension of such biomolecules fits properly with the range of distances between the nanowires to enable an efficient fluid separation.

The fluid separation structure may comprise at least one of the group consisting of a measurement apparatus, a fluid separation apparatus, a DNA separation apparatus, an electrophoresis apparatus, a biosensor, a lab-on-chip, a medical device, a portable device, a fluid purification system, and a life science apparatus. Thus, the fluid separation structure may be applied in any field in which the separation of different molecular structures is needed.

Thus, according to an exemplary embodiment, a fluid separation structure for separating DNA components of a fluidic sample by electrophoresis may be provided with an efficient separation medium formed by an array of nanowires.

For any method step, any conventional procedure as known from semiconductor technology may be implemented. Forming layers or components may include deposition techniques like CVD (chemical vapour deposition), PECVD (plasma enhanced chemical vapour deposition), ALD (atomic layer deposition), or sputtering. Removing layers or components may include etching techniques like wet etching, vapour etching, etc., as well as patterning techniques like optical lithography, UV lithography, electron beam lithography, etc.

Embodiments of the invention are not bound to specific materials, so that many different materials may be used. For conductive fluid separation structures, it may be possible to use metallization fluid separation structures, silicide fluid separation structures or polysilicon fluid separation structures. For semiconductor regions or components, crystalline silicon may be used. For insulating portions, silicon oxide or silicon nitride may be used.

The fluid separation structure may be formed on a purely crystalline silicon wafer or on an SOI wafer (Silicon On Insulator).

Any process technologies like CMOS, BIPOLAR, and BICMOS may be implemented.

The aspects defined above and further aspects of the invention are apparent from the examples of embodiment to be described hereinafter and are explained with reference to these examples of embodiment.

BRIEF DESCRIPTION OF THE DRAWINGS

The invention will be described in more detail hereinafter with reference to examples of embodiment but to which the invention is not limited.

DESCRIPTION OF EMBODIMENTS

Figure 1:
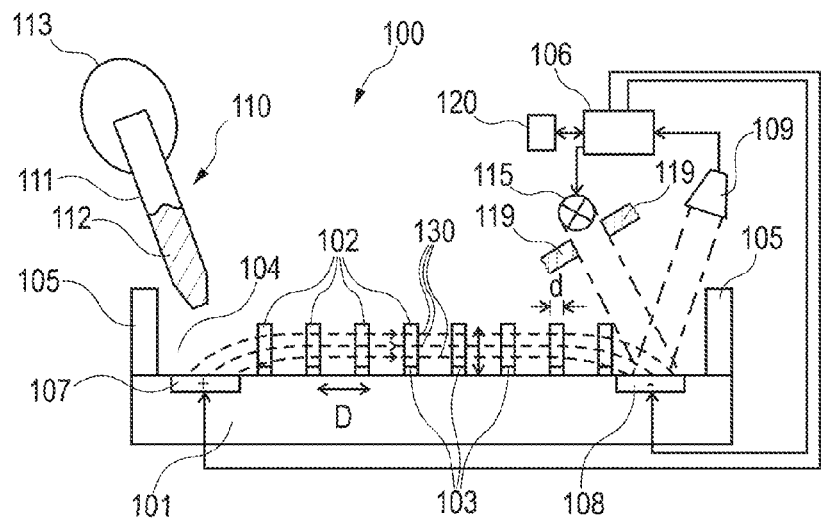
FIG. 1 illustrates a fluid separation apparatus according to an exemplary embodiment of the invention.

The illustration in the drawing is schematical. In different drawings, similar or identical elements are provided with the same reference signs.

In the following, referring to FIG. 1, a fluid separation apparatus 100 according to an exemplary embodiment of the invention will be explained.

The fluid separation apparatus 100 comprises a silicon substrate 101 such as a silicon wafer. A plurality of nanowires 102 are vertically grown in rows and columns, that is to say in a two-dimensional configuration, on a surface of the substrate 101, more particularly on catalyst spots 103 which have previously been formed by a deposition technique on a surface of the substrate 101.

As can be taken from FIG. 1, a sample reservoir 104 is defined by the main surface of the substrate 101 as well as by lateral sidewalls 105 delimiting the structure.

FIG. 1 schematically illustrates a pipette 110 having a capillary 111 and a fluidic sample 112 filled in the capillary 111. By manually actuating a rubber actuator 113, the fluidic sample 112 may be injected into the reservoir 104 for subsequent separation of the components of the fluidic sample 112. As an alternative to a pipette 110, the fluidic sample 112 may also be delivered in the sample reservoir 104 using a fluid supply system including fluid channels that may for instance be formed in the substrate 101.

The fluid separation apparatus 100 further comprises a control unit 106 such as a CPU (central processing unit) or a microprocessor. The CPU 106 may, for instance, serve as a voltage supply unit for supplying electric voltages to a first electrode 107 and to a second electrode 108 which are, in the present embodiment, integrated in a surface portion of the silicon substrate 101. According to other embodiments, the electrodes 107, 108 are provided apart from the substrate 101 (for instance may be located on inner surface portions of the walls 105). By applying appropriate voltages or electric potentials to the electrodes 107, 108, an electric field 130 may be generated within the fluid reservoir 104 so as to move electrically charged or polarisable particles along the array of the nanowires 102 (for instance from left to right).

Furthermore, a light source 115 (for instance a light emitting diode or a laser) and a light detector 109 are provided which can be also under the control of the control unit 106. The light source 115 may emit a light beam (which may be spatially delimited by an aperture 109) onto a surface of the substrate 101 at which the fractions of the fluidic sample 112 have passed the main way between the electrodes 107, 108, and are therefore separated. In such a surface portion of the substrate 101, an interaction between the light beam emitted by the light source 115 and (optional fluorescence labels attached to) particles of the fluidic sample 112 may occur. Thus, fluorescence light of a specific wavelength may be reemitted by the particles (or by their labels) of a specific fraction and may be detected by the detector 109 such as a photodiode or a CCD array. Therefore, the presence/absence and/or concentration of a specific fraction of the particles may be measured by the intensity of the light received by the detection unit 109. Such a detection signal may be transmitted to the CPU 106 for further evaluation or for output to a user.

As can be taken from FIG. 1, a diameter "d" of the nanowires may be in the order of magnitude of some 10 nm, whereas a length L of the nanowires 102 may be much larger than d, for instance may be 15 µm. Therefore, the nanowires 102 may be oblong nanowires having an aspect ratio which is significantly larger than one.

Furthermore, as can be taken from FIG. 1, an input/output unit 120 is provided which is bidirectionally coupled to the CPU 106. Via the input/output unit 120, a user may input commands or may receive results of a detection experiment. Thus, the input/output unit 120 may comprise a display unit such as an LCD display, and may comprise input elements such as a button, a keypad, a joystick, or even a microphone of a voice recognition system.

Figure 2:
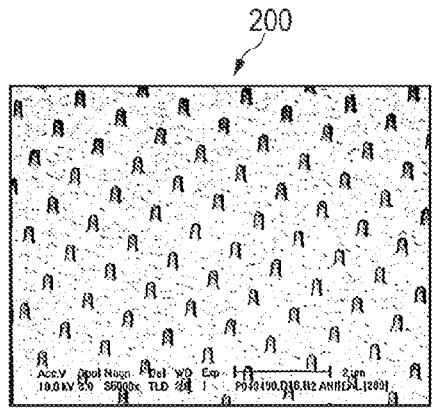
FIG. 2 to FIG. 4 illustrate examples of patterned surfaces of silicon nanopillars with different pitches that can be used for separation of DNA.
Figure 3:
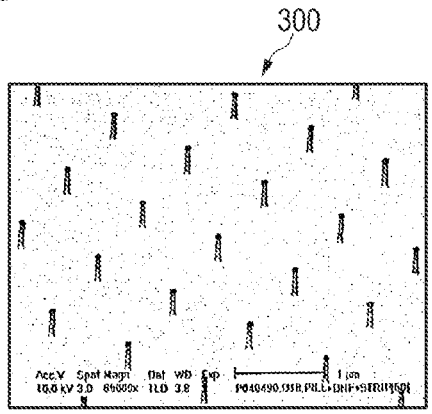
Figure 4:
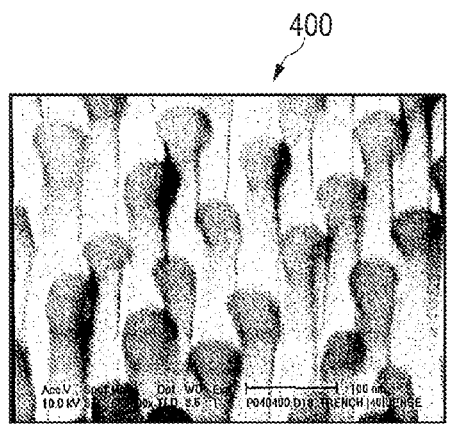

FIG. 2 to FIG. 4 show images 200, 300 and 400, respectively illustrating patterned and tailored DNA separation surfaces. These have been fabricated on a silicon substrate.

More particularly, FIG. 2 to FIG. 4 show examples of tailored patterned surfaces of silicon nanopillars with different pitches that can be properly used for separation of DNA. FIG. 2 shows an example of a wide pitch between silicon pillars, having a distance of approximately 2 µm.

FIG. 3 illustrates an example with a wider pitch than FIG. 2.

FIG. 4 shows an example of a narrow pitch pattern surface, with a distance in the order of magnitude of 100 nm.

In the following, referring to FIG. 5 to FIG. 7, a method of manufacturing a fluid separation structure according to an exemplary embodiment of the invention will be explained.

Figure 5:
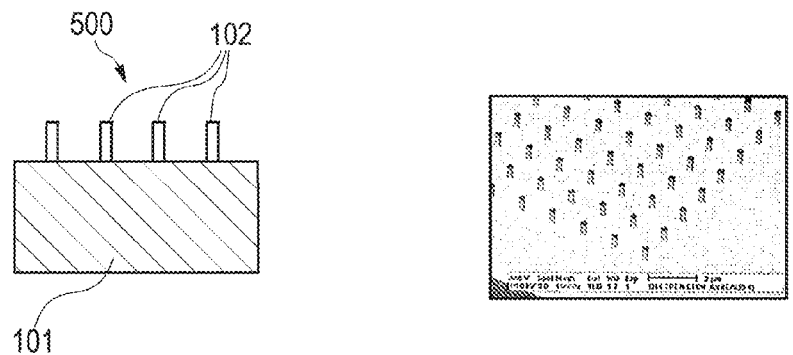
FIG. 5 to FIG. 7 illustrate a procedure of fabricating a fluid separation apparatus according to an exemplary embodiment of the invention.

As can be taken from FIG. 5, growing nanowires 102 on a surface of a silicon substrate 101 forms a layer sequence 500. In other words, in FIG. 5, the nanowires 102 can be grown and dry etched using a conventional method.

Figure 6:
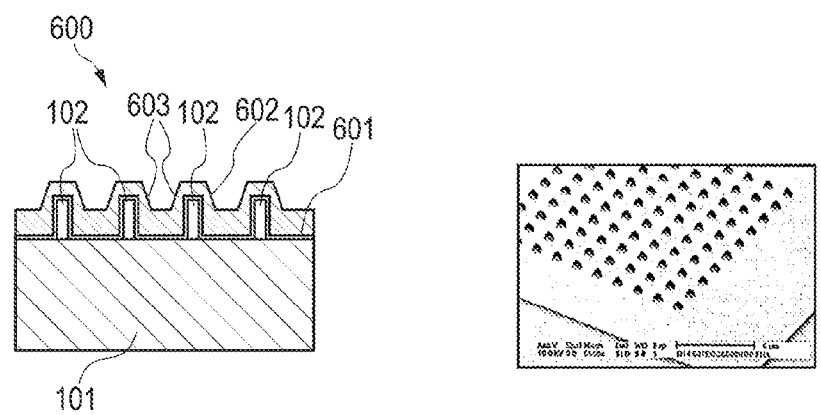

As can be taken from FIG. 6 showing a layer sequence 600, a TEOS layer (Tetra Ethyl Ortho Silicate) 601 is uniformly deposited on the layer sequence 500. This TEOS layer 601 is a silicon oxide layer. In other words, a thin layer 601 of silicon oxide is deposited using CVD (chemical vapour deposition) and TEOS (Tetra Ethyl Ortho Silicate) as source material. In the described example, the layer 601 is 10 nm thick, and this thickness is substantially the same at every location. The function of this layer 601 is to form an anchor and a protective shield for the thin pillars 102 against sputtering in a subsequent deposition process of an insulating layer 602 of, again, silicon dioxide ($SiO_2$).

However, the deposition is now performed using a High-Density Plasma deposition. In this process, a simultaneous deposition and sputtering takes place, the deposition prevailing. Such a specific deposition process has a self-planarizing property, since the thickness of the insulating layer 602 is thinner on top of the pillars 102 than in the bordering regions. In this example, the thickness on top of the pillars 102 may be about 100 nm. Typical for the deposition process used is also that a tapering 603 is obtained in the insulating layer 602 alongside the pillar 102, corresponding with a, for instance, 45° side wall angle. In FIG. 6, a thin layer 601 of TEOS is deposited on the nanowires 102 array followed by a High-Density Plasma (HDP) oxide 602 deposition.

Figure 7:
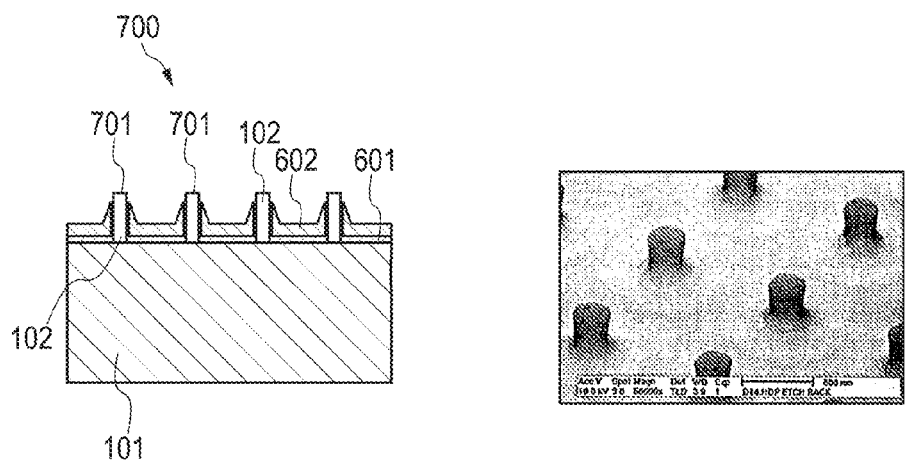

Next, see a layer sequence 700 shown in FIG. 7, parts of the insulating layer 601 and of the further insulating layer 602 on top of the pillar 102 are removed by an etching procedure that is selective towards silicon and comprises in this example an etching on the basis of hydrogen fluoride, possibly buffered. The etching may be done on a time base using a known etching rate.

By taking this measure, tips 701 of the nanowires 102 are exposed. In FIG. 7, the tips 701 of the nanowires 102 are exposed after an etch-back-step removing silicon oxide material from the top of the nanowires 102.

Figure 8:
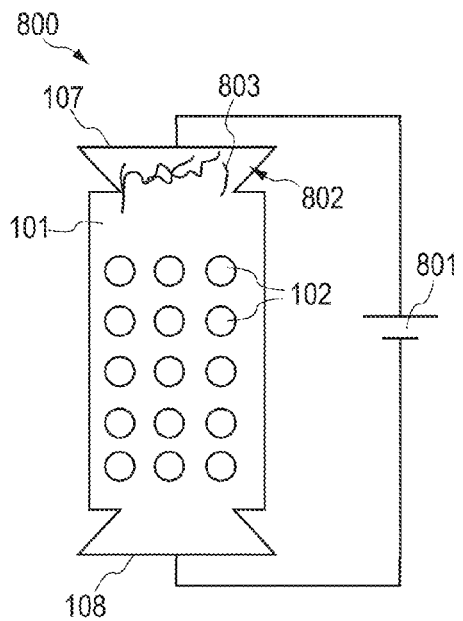
FIG. 8 to FIG. 10 illustrate fluid separation devices according to exemplary embodiments of the invention.

FIG. 8 shows a top view of a fluid separation structure 800 according to an exemplary embodiment of the invention. In particular FIG. 8 shows a fluid separation structure 800 in which two electrodes 107, 108 can be powered by a current source 801 to generate an electric field. Under the influence of such an electric field, DNA molecules 803 provided in a buffer solution 802 containing the DNA strains 803 of different lengths may be transported under the influence of an electric force through the matrix-like array of nanopillars 102. However, in the operation mode of FIG. 8, no electric field is applied to the electrodes 107, 108 so that the DNA molecules 803 do not move under the influence of an electric field.

Figure 9:
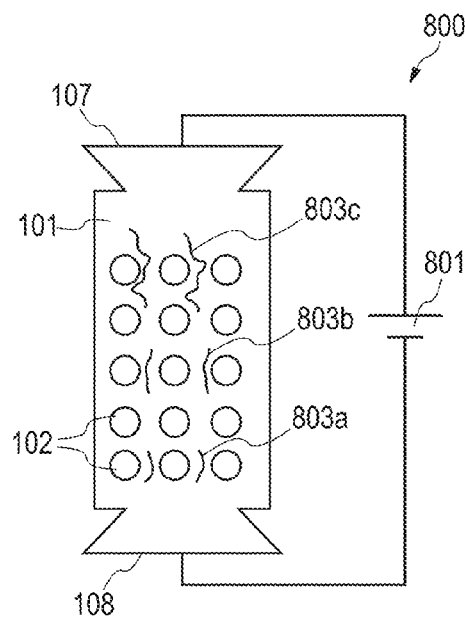

FIG. 9 shows another operation state of the device 800 in which an electric field has already been applied between the electrodes 107, 108 to set the charge particles 803 in motion. First charged particles 803a are relatively small so that they can easily pass the spaces between the pillars 102. Second charged particles 803b are larger and are therefore slower when passing between the pillars 102. Third charged particles 803c are the largest fraction and therefore the slowest regarding motion.

In FIG. 8, the electric field generated by the current source 801 is off, wherein the electric field is on in FIG. 9. Therefore, in FIG. 9, the DNA strains 803a to 803c of different lengths are sorted out due to the patterned surface of the device 800. Thus, FIG. 8 and FIG. 9 show an example of the use of the patterned surface in DNA separation by electrophoresis. In FIG. 8, the electric field is off and different strains of DNA 803 are loaded in the buffer solution 802. In FIG. 9, the electric field is on and the DNA fragments 803a to 803c are separated according to their mobilities with respect to the geometrical parameters.

The mobility of DNA depends among other factors on the length of the DNA strains. According to an exemplary embodiment of the invention, the migration speed of DNA is effected by the pillar size and spacing. Since embodiments of the invention allow for the appropriate adjustment of such geometrical parameters, it is also possible to extend the separation range of DNA lengths as compared to conventional separation techniques.

Figure 10:
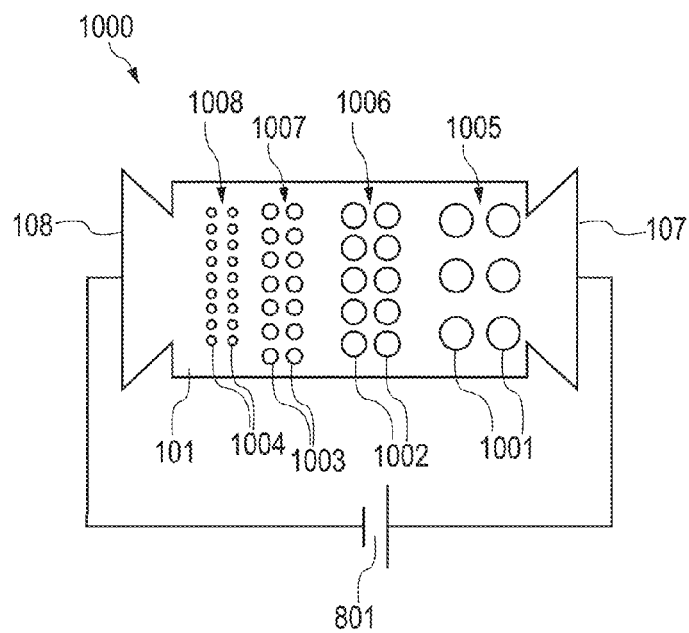

FIG. 10 shows a fluid separation device 1000 according to another exemplary embodiment of the invention. The device 1000 is adapted for a massive separation parallelism.

In the embodiment of FIG. 10, a two-dimensional array of nanowires 1001 to 1004 comprises first to fourth portions 1005 to 1008. A distance between adjacent nanowires 1001 to 1004 in different ones of the plurality of portions 1005 to 1008 are different (at least a distance in a direction perpendicular to a motion direction of the sample between the electrodes 107, 108). Moreover, a diameter of nanowires 1001 to 1004 in different ones of the plurality of portions 1005 to 1008 is different.

Therefore, the first portion 1005 comprises nanowires 1001 having a very large diameter and a very large difference from one another. In the second portion 1006, nanowires 1002 have a smaller diameter and a smaller distance from one another. In a third portion 10007, nanowires 1003 have a further reduced diameter. In a fourth portion 1008, nanowires 1004 have a further reduced diameter.

Therefore, in the device 1000, the surface of the separation device 1000 can be composed of several sections 1005 to 1008 wherein any of geometry parameters can be changed according to user needs.

Finally, it should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. In a device claim enumerating several means, several of these means may be embodied by one and the same item of software or hardware. The mere fact that certain measures are recited in mutually different dependent claims does not indicate that a combination of these measures cannot be used to advantage.

The invention claimed is:

1. A fluid separation structure, the fluid separation structure comprising
    a substrate;
    at least one set of a plurality of nanowires grown on the substrate and configured and arranged to separate particles in a fluid based on respective sizes of particles contained in the fluid; and
    an insulating cover structure partially etched away for partially covering the at least one set of a plurality of nanowires so that tips of the at least one set of a plurality of nanowires are exposed.

2. The fluid separation structure according to claim 1, wherein the insulating cover structure is arranged to partially cover and to form partially tapered lateral side walls of the plurality of nanowires.

3. The fluid separation structure according to claim 1, wherein the insulating cover structure is arranged to partially cover a surface of the ubstrate, with tapered regions directed downward towards the substrate between the plurality of nanowires.

4. The fluid separation structure according to claim 1, wherein the insulating cover structure includes an electrically insulating material and is configured and arranged to provide different degrees of lateral support due to differing lateral thicknesses adjacent the plurality of nanowires.

5. The fluid separation structure according to claim 1, wherein the insulating cover structure comprises silicon oxide.

6. The fluid separation structure according to claim 1, wherein the insulating cover structure comprises a Tetra Ethyl Ortho Silicate silicon oxide material and a High-Density Plasma silicon oxide material.

7. The fluid separation structure of claim 1, wherein the at least one set of a plurality of nanowires includes a first set, a second set, and a third set of a plurality of nanowires.

8. The fluid separation structure of claim 1, wherein the at least one set of a plurality of nanowires includes a first set and a second set of a plurality of nanowires, and the first set of a plurality of nanowires has a first diameter, and the second set of a plurality of nanowires has a second diameter, and the second diameter is greater than the first diameter.

9. The fluid separation structure of claim 1, wherein the at least one set of a plurality of nanowires includes a first set, a second set, and a third set of a plurality of nanowires, the first set of a plurality of nanowires has a first diameter, the second set of a plurality of nanowires has a second diameter, and the third set of a plurality of nanowires has a third diameter, and wherein the second diameter is greater than the first diameter, and the third diameter is greater than the second diameter.

10. The fluid separation structure of claim 1, wherein the insulating cover structure includes hydrophobic and hydrophilic regions configured and arranged to facilitate passing of the particles in the fluid through the at least one set of a plurality of nanowires.

11. The fluid separation structure of claim 1, wherein the at least one set of a plurality of nanowires includes a first set, a second set, and a third set of a plurality of nanowires, each set having a different diameter and being arranged on the substrate in order of increasing diameter to facilitate a separation range of the particles in the fluid.

12. The fluid separation structure of claim 1, further including a layer including TEOS, configured and arranged on the substrate and between the insulating cover structure to provide support to the at least one set of a plurality of nanowires.

13. The fluid separation structure of claim 1, wherein each nanowire of the at least one set of a plurality of nanowires has a height, from a portion of the nanowire in contact with the substrate to the tip of the nanowire, between 5 μm and 50 μm.

14. The fluid separation structure of claim 1, wherein the insulating cover structure includes a lower portion near the substrate and an upper portion near the tips of the at least one set of a plurality of nanowires, the lower portion being thicker than the upper portion to support the plurality of nanowires.

15. The fluid separation structure of claim 14, wherein the upper portion of the insulating cover structure tapers to the lower portion of the insulating cover structure at approximately a 45 degree angle relative to the substrate.

16. A method of manufacturing a fluid separation structure, the method comprising
    growing a plurality of nanowires on a substrate at relative distances from one another to facilitate separation of particles in a fluid based on respective sizes of the particles;
    forming a cover structure covering the plurality of nanowires; and
    exposing a tip of the plurality of nanowires by removing a part of the cover structure.

* * * * *